United States Patent
Pan et al.

(10) Patent No.: US 11,931,324 B2
(45) Date of Patent: Mar. 19, 2024

(54) PHARMACEUTICAL COMPOSITION FOR PREVENTION OR TREATMENT OF OSTEOARTHRITIS COMPRISING OBTUSIFOLIN, DERIVATIVE THEREOF, OR PHARMACEUTICALLY ACCEPTABLE SALT THEREOF AS ACTIVE INGREDIENT

(71) Applicant: KOREA INSTITUTE OF SCIENCE AND TECHNOLOGY, Seoul (KR)

(72) Inventors: Cheol-ho Pan, Seoul (KR); Kwang-hyun Cha, Seoul (KR); Song Yi Koo, Seoul (KR); Eun Ha Lee, Seoul (KR); Hee Ju Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 17/689,665

(22) Filed: Mar. 8, 2022

(65) Prior Publication Data

US 2022/0323377 A1 Oct. 13, 2022

(30) Foreign Application Priority Data

Apr. 2, 2021 (KR) ........................ 10-2021-0043512

(51) Int. Cl.
*A61K 31/122* (2006.01)
*A23L 33/00* (2016.01)
*A23L 33/10* (2016.01)
*A61P 19/02* (2006.01)
*A61P 29/00* (2006.01)

(52) U.S. Cl.
CPC ............ *A61K 31/122* (2013.01); *A23L 33/10* (2016.08); *A23L 33/40* (2016.08); *A61P 19/02* (2018.01); *A61P 29/00* (2018.01); *A23V 2002/00* (2013.01)

(58) Field of Classification Search
None
See application file for complete search history.

(56) References Cited

U.S. PATENT DOCUMENTS 10,987,386 B2 4/2021 Kim et al.

FOREIGN PATENT DOCUMENTS

| CN | 1628741 A | 6/2005 |
|---|---|---|
| KR | 10-2011-0039762 A | 4/2011 |
| KR | 10-1090284 B1 | 12/2011 |
| KR | 10-2019-0137317 A | 12/2019 |
| KR | 10-2084227 B1 | 3/2020 |
| KR | 10-2098067 B1 | 4/2020 |

OTHER PUBLICATIONS

Hsu et al. Obtusifolin Suppresses Phthalate Esters-Induced Breast Cancer Bone Metastasis by Targeting Parathyroid Hormone-Related Protein. J. Agric. Food Chem. 2014, 62, 11933-11940.*
He et al., "Anti-allodynic Effects of Obtusifolin and Gluco-Obtusifolin against Inflammatory and Neuropathic Pain: Possible Mechanism for Neuroinflammation", Biol. Pharm. Bull., vol. 37, No. 10, pp. 1606-1616, (2014).
Nam et al., "Obtusifolin, an Anthraquinone Extracted from *Senna obtusifolia* (L.) H.S.Irwin & Barneby, Reduces Inflammation in a Mouse Osteoarthritis Model", Pharmaceuticals 2021, 14, 249, pp. 1-10.

* cited by examiner

*Primary Examiner* — Samantha L Shterengarts
(74) *Attorney, Agent, or Firm* — Birch, Stewart, Kolasch & Birch, LLP

(57) ABSTRACT

Provided is a pharmaceutical composition for preventing or treating osteoarthritis, the pharmaceutical composition including, as an active ingredient, obtusifolin, a derivative thereof, or a pharmaceutically acceptable salt thereof. The composition according to an aspect inhibits cartilage destruction-promoting factors and alleviates inflammatory responses, thereby exhibiting significantly excellent effects for preventing or treating osteoarthritis.

1 Claim, 13 Drawing Sheets

Specification includes a Sequence Listing.

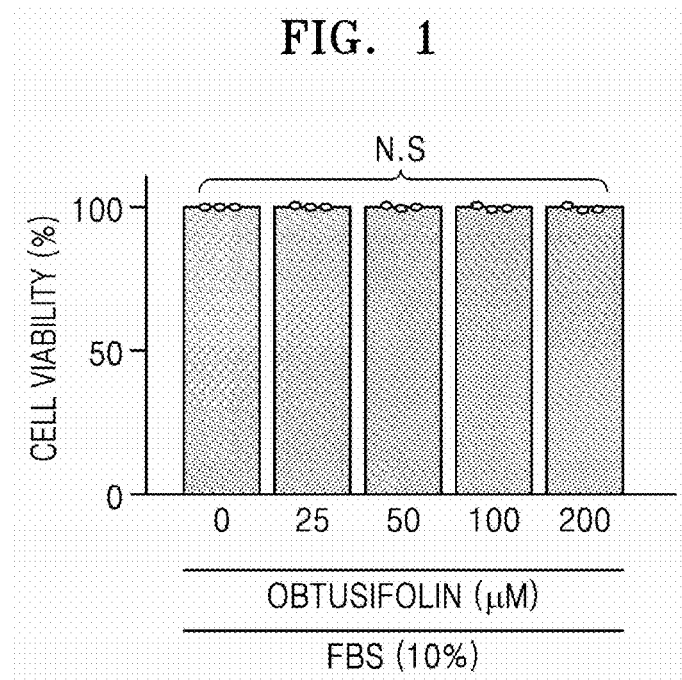

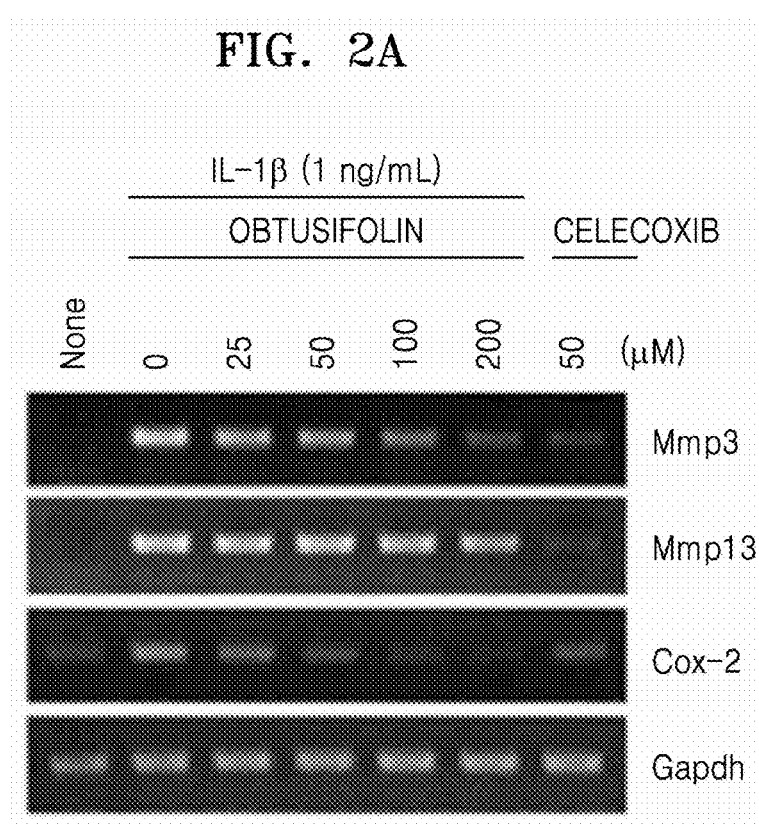

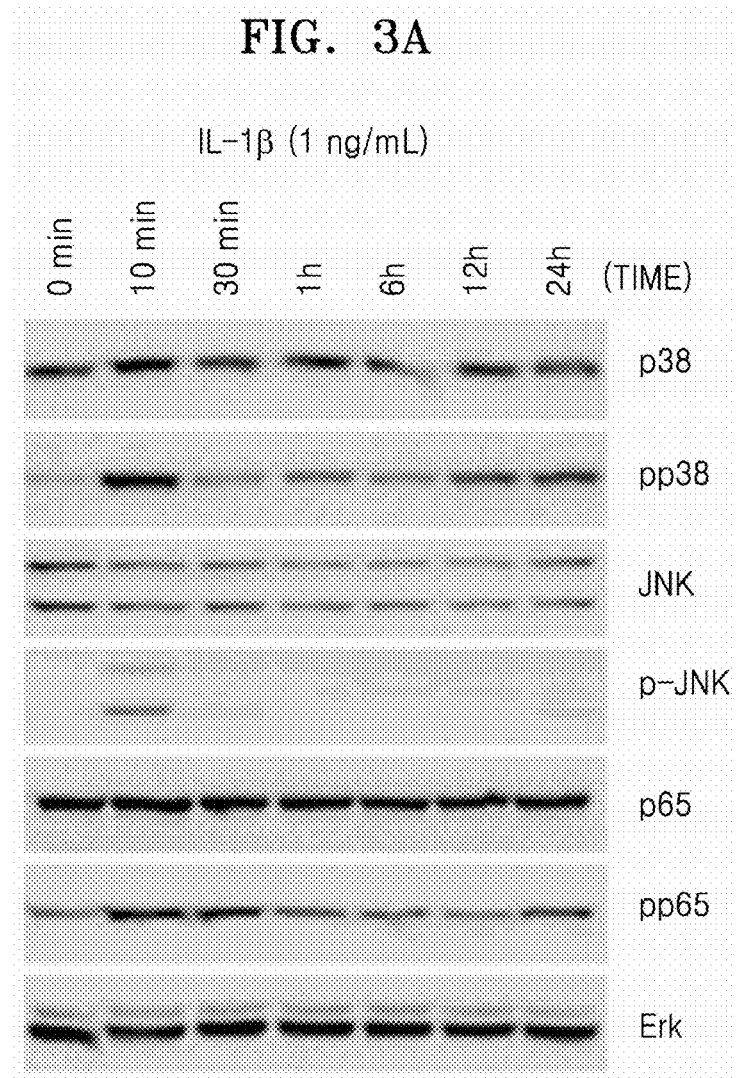

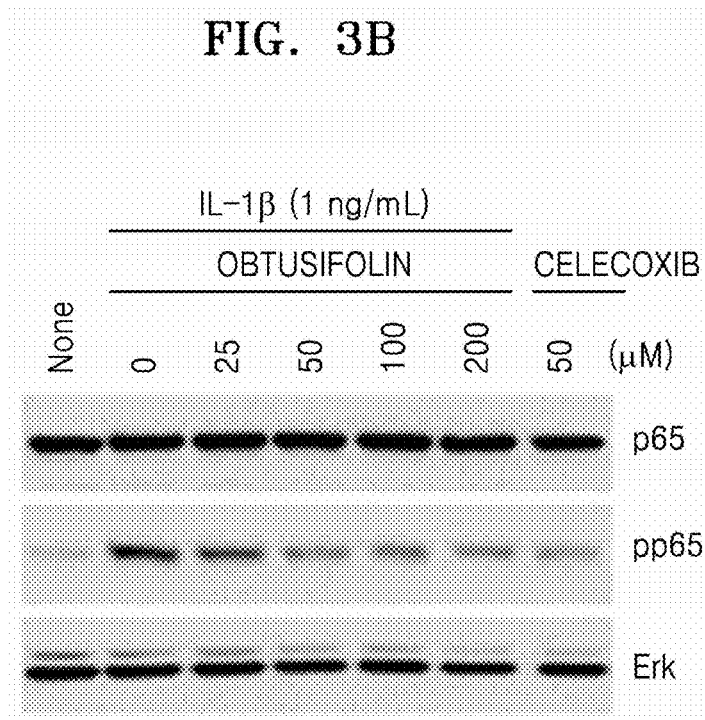

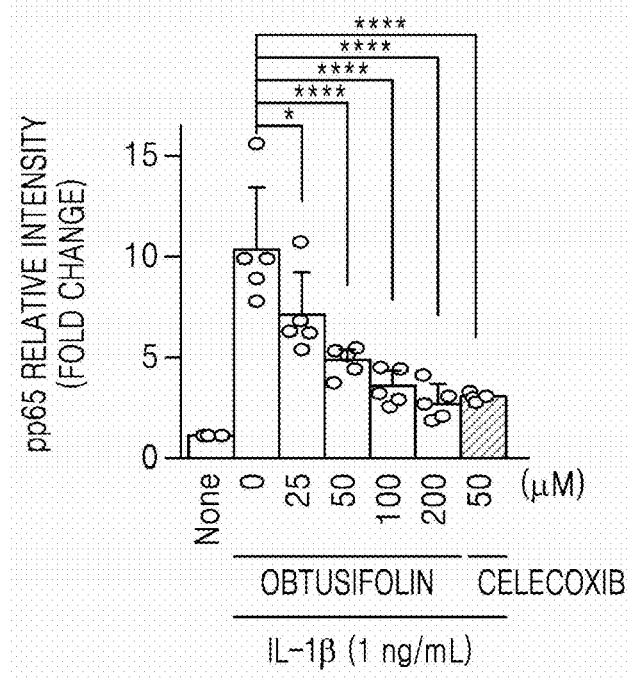

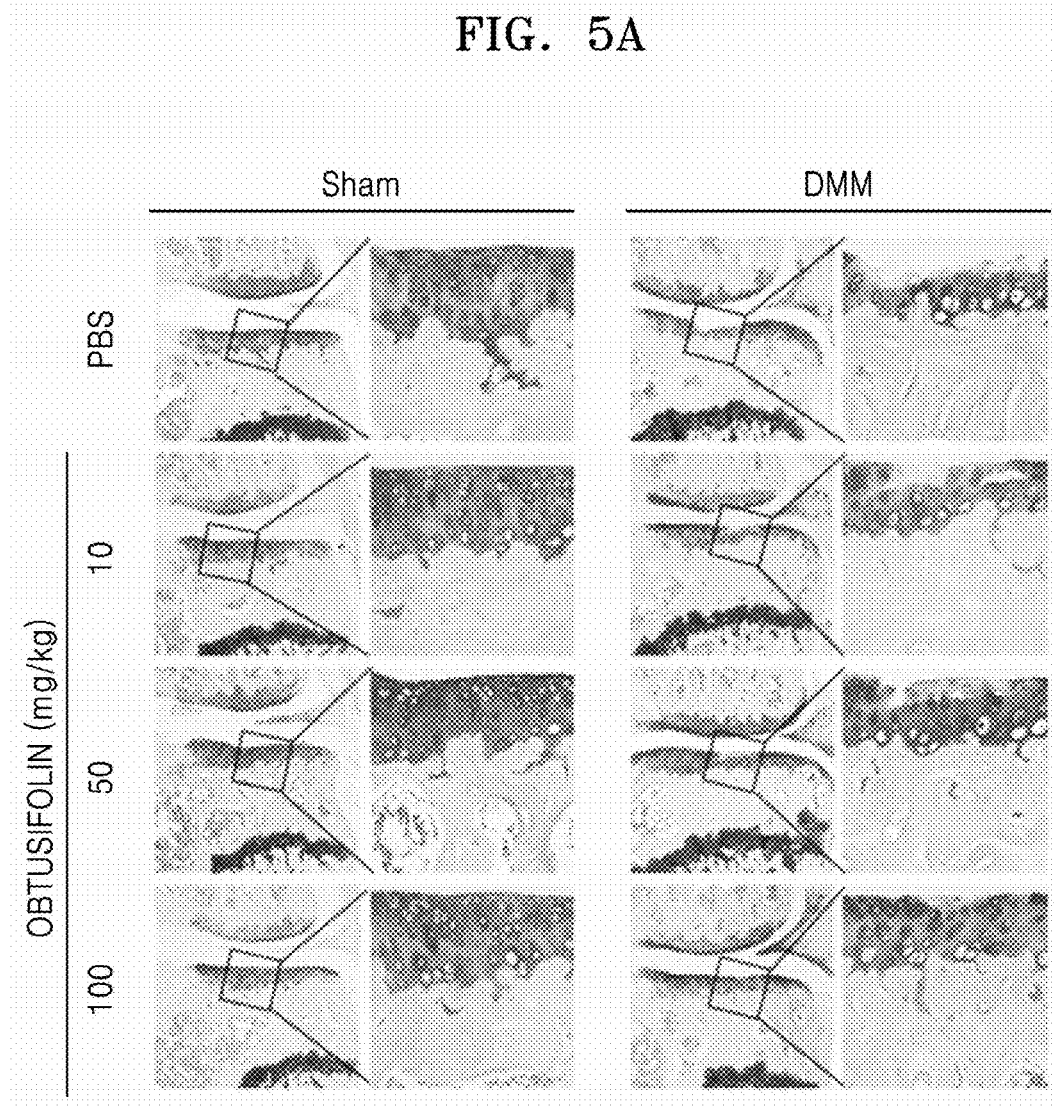

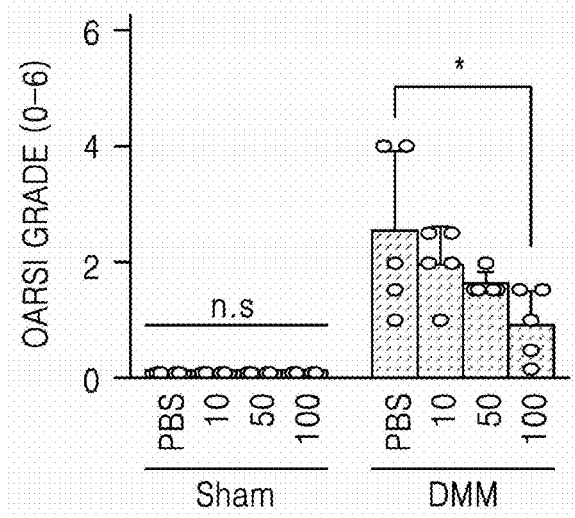

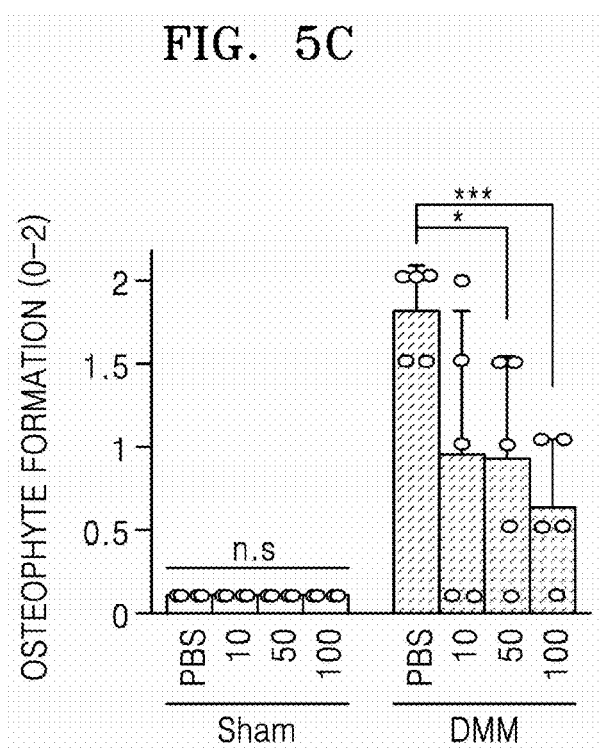

SEQUENCE LISTING

<160> NUMBER OF SEQ ID NOS: 14

<210> SEQ ID NO 1
<211> LENGTH: 27
<212> TYPE: DNA
<213> ORGANISM: Artificial Sequence
<220> FEATURE:
<223> OTHER INFORMATION: MMP3 Primer - S

<400> SEQUENCE: 1
ctgtgtgtgg ttgtgtgctc atcctac                                27

<210> SEQ ID NO 2
<211> LENGTH: 27
<212> TYPE: DNA
<213> ORGANISM: Artificial Sequence
<220> FEATURE:
<223> OTHER INFORMATION: MMP3 Primer - AS

<400> SEQUENCE: 2
ggcaaatccg gtgtataatt cacaatc                                27

<210> SEQ ID NO 3
<211> LENGTH: 23
<212> TYPE: DNA
<213> ORGANISM: Artificial Sequence
<220> FEATURE:
<223> OTHER INFORMATION: MMP13 Primer - S

<400> SEQUENCE: 3
tgatggacct tctggtcttc tgg                                    23

<210> SEQ ID NO 4
<211> LENGTH: 23
<212> TYPE: DNA
<213> ORGANISM: Artificial Sequence
<220> FEATURE:
<223> OTHER INFORMATION: MMP13 Primer - AS

<400> SEQUENCE: 4
catccacatg gttgggaagt tct                                    23

<210> SEQ ID NO 5
<211> LENGTH: 23
<212> TYPE: DNA
<213> ORGANISM: Artificial Sequence
<220> FEATURE:
<223> OTHER INFORMATION: COX2 Primer - S

<400> SEQUENCE: 5
ggtctggtgc ctggtctgat gat                                    23

<210> SEQ ID NO 6
<211> LENGTH: 22
<212> TYPE: DNA
<213> ORGANISM: Artificial Sequence
<220> FEATURE:
<223> OTHER INFORMATION: COX2 Primer - AS

<400> SEQUENCE: 6
gtcctttcaa ggagaatggt gc                                     22

<210> SEQ ID NO 7
<211> LENGTH: 19
<212> TYPE: DNA
<213> ORGANISM: Artificial Sequence

```
<220> FEATURE:
<223> OTHER INFORMATION: Gapdh Primer - S

<400> SEQUENCE: 7
tcactgccac ccagaagac                                              19

<210> SEQ ID NO 8
<211> LENGTH: 19
<212> TYPE: DNA
<213> ORGANISM: Artificial Sequence
<220> FEATURE:
<223> OTHER INFORMATION: Gapdh Primer - AS

<400> SEQUENCE: 8
tgtaggccat gaggtccac                                              19

<210> SEQ ID NO 9
<211> LENGTH: 21
<212> TYPE: DNA
<213> ORGANISM: Artificial Sequence
<220> FEATURE:
<223> OTHER INFORMATION: qMMP3 Primer - S

<400> SEQUENCE: 9
tcctgatgtt ggtggcttca g                                           21

<210> SEQ ID NO 10
<211> LENGTH: 21
<212> TYPE: DNA
<213> ORGANISM: Artificial Sequence
<220> FEATURE:
<223> OTHER INFORMATION: qMMP3 Primer - AS

<400> SEQUENCE: 10
tgtcttggca atccggtgt a                                            21

<210> SEQ ID NO 11
<211> LENGTH: 23
<212> TYPE: DNA
<213> ORGANISM: Artificial Sequence
<220> FEATURE:
<223> OTHER INFORMATION: qMMP13 Primer - S

<400> SEQUENCE: 11
cttcttcttg ttgagctgga ctc                                         23

<210> SEQ ID NO 12
<211> LENGTH: 21
<212> TYPE: DNA
<213> ORGANISM: Artificial Sequence
<220> FEATURE:
<223> OTHER INFORMATION: qMMP13 Primer - AS

<400> SEQUENCE: 12
ctgtggaggt cactgtagac t                                           21

<210> SEQ ID NO 13
<211> LENGTH: 22
<212> TYPE: DNA
<213> ORGANISM: Artificial Sequence
<220> FEATURE:
<223> OTHER INFORMATION: qCOX2 Primer - S

<400> SEQUENCE: 13
ttcaacacac tctatcactg gc                                          22
```

```
<210> SEQ ID NO 14
<211> LENGTH: 21
<212> TYPE: DNA
<213> ORGANISM: Artificial Sequence
<220> FEATURE:
<223> OTHER INFORMATION: qCOX2 Primer - AS

<400> SEQUENCE: 14
agaagcgttt gcggtactca t                                        21
```

PHARMACEUTICAL COMPOSITION FOR PREVENTION OR TREATMENT OF OSTEOARTHRITIS COMPRISING OBTUSIFOLIN, DERIVATIVE THEREOF, OR PHARMACEUTICALLY ACCEPTABLE SALT THEREOF AS ACTIVE INGREDIENT

CROSS-REFERENCE TO RELATED APPLICATION

This application is based on and claims priority under 35 U.S.C. § 119 to Korean Patent Application No. 10-2021-0043512, filed on Apr. 2, 2021, in the Korean Intellectual Property Office, the disclosure of which is incorporated by reference herein in its entirety.

BACKGROUND

1. Field

The present disclosure relates to a pharmaceutical composition for preventing or treating osteoarthritis, the pharmaceutical composition including, as an active ingredient, obtusifolin, a derivative thereof, or a pharmaceutically acceptable salt thereof.

2. Description of the Related Art

Arthritis refers to abnormalities in joints. Arthritis may be in many forms, from minor to severe forms, and does not always get worse. An arthritis-related disease is a representative degenerative and incurable disease from which about 12% of the world population suffers, and there are more than about 2 million patients in Korea. Arthritis is a generic name for inflammatory changes in the musculoskeletal and connective tissues of the body, resulting in general symptoms in the musculoskeletal system. Such a disease is characterized by chronic inflammation often causing permanent tissue damage, deformities, degeneration, and disability by affecting joints, bones, cartilage tissue, or spinal cord.

Types of arthritis include osteoarthritis, rheumatoid arthritis, ankylosing spondylitis, reactive arthritis, psoriatic arthritis, systemic lupus erythematosus, polymyositis, polymyalgia rheumatica, and the like.

Degenerative arthritis or wear-and-tear arthritis, also called osteoarthritis, is the most common arthritis mainly occurring in middle age or old age, and refers to arthritis affecting the joints of the spine and lower extremities (e.g., coxae, knees, and foot joints). When ordinary people are in their 60 s or 70 s, more than about 60% of the people becomes susceptible to osteoarthritis. Osteoarthritis is a common disease that may affect everyone with age. It is common in people over 60, but is more common in men than in women up to the age of 45, and more frequently occurs in women over the age of 55. Causes of osteoarthritis may be largely classified according to whether osteoarthritis is primary or secondary. Deterioration symptoms, i.e., degenerative changes, in normal articular cartilage due to frailty without a specific cause are regarded as primary causes, which commonly occur in women. The exact cause and etiology of primary osteoarthritis are unknown. Causes of secondary osteoarthritis may be largely classified by joint damage, abnormal cartilage matrix, deformation of the subchondral bone, and the like.

Rheumatoid arthritis is the most common type of inflammatory arthritis, affecting about 1% to 2% of the population. Rheumatoid arthritis is caused by inflammation of the synovial joints and may occur to anyone in teens or older. However, it is more common in women, especially among those between the ages of 30 and 50.

Ankylosing spondylitis is caused by inflammation of the joints connecting the spine and pelvis. Occasionally, it may occur in the hips. Ankylosing spondylitis is about 3 times more common in men than in women, and occurs mainly to people between the ages of 20 and 40. For those having a parent or sibling with the disease, the risk of developing the disease is about 20 times higher.

Systemic lupus erythematosus is one of the diseases called connective tissue diseases. Systemic lupus erythematosus is similar to rheumatoid arthritis in that it is an autoimmune disease. However, it occurs much more rarely and is usually less severe than rheumatoid arthritis. About 90% of people who have this disease are young women in their 20 s to 40 s.

Treatments of arthritis may include drug therapy, exercise therapy, surgical therapy, and the like. Regarding drug therapy among these treatments, drugs, such as analgesics, adrenocortical hormone drugs, nonsteroidal anti-inflammatory drugs, and the like, which relieve pain by treating inflammation, are being used. However, essentially there is still no drug to treat arthritis. Analgesics have a mechanism of relieving pain, but do not have an anti-inflammatory effect. In addition, although an anti-inflammatory agent has a mechanism of reducing inflammation, problems have been reported in terms of pharmacological action methods and potential side effects. Thus, to minimize side effects, the development of therapeutic agents derived from natural products for arthritis continues (Korean Patent Registration Number: 10-2098067).

However, the development of a therapeutic agent capable of treating osteoarthritis essentially by simultaneously exhibiting an anti-inflammatory effect as well as an effect of promoting cartilage generation or inhibiting cartilage destruction is still insufficient.

Under this background, the inventors of the present disclosure completed the present application by confirming effects of obtusifolin on alleviation of inflammatory response and inhibition of cartilage destruction through remarkably excellent inhibition of NF-κB signal transduction, and accordingly by confirming the use of obtusifolin for preventing or treating osteoarthritis.

SUMMARY

One or more embodiments include a pharmaceutical composition for preventing or treating osteoarthritis, the pharmaceutical composition comprising, as an active ingredient, obtusifolin, a derivative thereof, or a pharmaceutically acceptable salt thereof.

One or more embodiments include a food composition for improving or preventing osteoarthritis, the food composition comprising, as an active ingredient, obtusifolin, a derivative thereof, or a pharmaceutically acceptable salt thereof.

One or more embodiments include a composition for anti-inflammation, inhibition of cartilage destruction, inhibition of osteophyte formation, or inhibition of subchondral bone formation, the composition comprising, as an active ingredient, obtusifolin, a derivative thereof, or a pharmaceutically acceptable salt thereof.

One or more embodiments include a method for preventing or treating osteoarthritis, the method comprising administering obtusifolin, a derivative thereof, or a pharmaceutically acceptable salt thereof to a subject.

One or more embodiments include a method for inhibiting inflammation, inhibiting cartilage destruction, inhibiting osteophyte formation, or inhibiting subchondral bone formation, the method comprising administering obtusifolin, a derivative thereof, or a pharmaceutically acceptable salt thereof to a subject.

Other purposes and advantages of the present disclosure will become more obvious with the following detailed description, claims, and drawing. Contents not described herein will be sufficiently recognized and inferred by those skilled in the technical field of the present application or in a similar technical field therewith, and thus descriptions of such contents will be omitted.

Additional aspects will be set forth in part in the description which follows and, in part, will be apparent from the description, or may be learned by practice of the presented embodiments of the disclosure.

Description and embodiments disclosed herein may also be applied to other descriptions and embodiments, respectively. That is, all combinations of various elements disclosed herein belong to the scope of the present disclosure. In addition, the scope of the present application is not construed to be limited by the detailed description provided below.

An aspect provides a pharmaceutical composition for preventing or treating osteoarthritis, the pharmaceutical composition comprising, as an active ingredient, obtusifolin, a derivative thereof, or a pharmaceutically acceptable salt thereof.

The obtusifolin may be a compound having a structure of Formula 1:

Formula 1

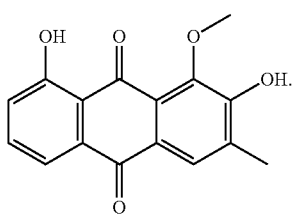

The obtusifolin may have a molecular formula or $C_{16}H_{12}O_5$ and a molecular weight in a range of about 280 g/mol to about 290 g/mol. In addition, the obtusifolin may be a single compound derived from a natural product.

The term "derivative" as used herein refers to a compound having changes to the extent that the structure and properties of the parent are not significantly changed due to introduction, substitution, oxidation, reduction, or the like of a functional group of obtusifolin. Types of such a functional group are not limited, and examples thereof are each independently: a $C_1$-$C_{20}$ bicyclic hydrocarbon group unsubstituted or substituted with a hydroxy group, a phenoxy group, a thienyl group, a furyl group, a pyridyl group, a cyclohexyl group, an alkylalcohol group, an alkyldialcohol group, or a substituted or unsubstituted phenyl group; a $C_3$-$C_{30}$ cyclichydrocarbon group unsubstituted or substituted with a hydroxy group, a hydroxymethyl group, a methyl group, or an amino group; or a sugar moiety. However, the functional group is not limited thereto.

The term "sugar moiety" as used herein refers to a group in which one hydrogen atom is removed from a polysaccharide molecule, and thus may refer to, for example, a moiety derived from a monosaccharide or an oligosaccharide.

The term "substituted" as used herein refers to, unless otherwise defined, one or more hydrogen atom of the functional group is substituted with a halogen atom (e.g., F, Cl, Br, or I), a hydroxy group, a nitro group, a cyano group, an imino group (e.g., =NH or =NR, wherein R may be a $C_1$-$C_{10}$ alkyl group), an amino group (e.g., —NH2, —NH (R'), or —N(R")(R'"), wherein R', R", and R'" may each independently a $C_1$-$C_{10}$ alkyl group), an amidino group, a hydrazine group, a hydrazone group, a carboxylic acid group, a $C_1$-$C_{20}$ alkyl group, a $C_6$-$C_{30}$ aryl group, a $C_3$-$C_{30}$ cycloalkyl group, a $C_3$-$C_{30}$ heteroaryl group, or a $C_2$-$C_{30}$ heterocycloalkyl group.

The term "pharmaceutically acceptable salt" as used herein refers to any salt that retains desired biological and/or physiological activity of the compound and that exhibits the least undesired toxicological effect. For use as the salt, an acid addition salt formed with a pharmaceutically acceptable free acid may be utilized. The acid addition salt may be prepared by methods in the art, for example, by dissolving a compound in an excessive acid aqueous solution and precipitating a salt using a water-miscible organic solvent such as methanol, ethanol, acetone, or acetonitrile. Equal molar amounts of a compound and an acid or alcohol (e.g., glycol monomethyl ether) in water may be heated. Then, the mixture may be dried by evaporation, or the precipitated salt may be subjected to suction-filtration. Here, for use as the free acid, an inorganic acid and an organic acid may be used. Examples of the inorganic acid are hydrochloric acid, hydrobromic acid, phosphoric acid, nitric acid, sulfuric acid, tartaric acid, and the like, and examples of the organic acid are methane sulfonic acid, p-toluene sulfonic acid, acetic acid, trifluoroacetic acid, maleic acid, succinic acid, oxalic acid, benzoic acid, tartaric acid, fumaric acid, manderic acid, propionic acid, citric acid, lactic acid, glycollic acid, gluconic acid, galacturonic acid, glutamic acid, glutaric acid, glucuronic acid, aspartic acid, ascorbic acid, carbonic acid, vanillic acid, hydroiodic acid, and the like. However, the inorganic acid and the organic acid are not limited thereto.

In addition, a pharmaceutically acceptable metal salt may be prepared using a base. An alkali metal or an alkaline earth metal salt may be, for example, obtained by dissolving the compound in a solution containing an excess of alkali metal hydroxide or alkaline earth metal hydroxide, filtering an undissolved compound salt, and then drying the filtrate by evaporation. Here, as a metal salt, it is pharmaceutically suitable to prepare a sodium salt, a potassium salt, or a calcium salt, but is not limited thereto.

The pharmaceutically acceptable salt of the obtusifolin may include, unless otherwise indicated, almost any salt of an acidic or basic group that may be present in the obtusifolin. For example, the pharmaceutically acceptable salt may include sodium, calcium, and potassium salts of a hydroxyl group, and other pharmaceutically acceptable salts of the amino group may include hydrobromide, sulfate, hydrogen sulfate, phosphate, hydrogen phosphate, dihydrogen phosphate, acetate, succinate, citrate, tartrate, lactate, mandelate, methanesulfonate (mesylate), and p-toluenesulfonate (tosylate) salts. The salts may be prepared by methods of preparing salts known in the art. Preferably, the pharmaceutically acceptable salt of the obtusifolin may include a sodium salt, but is not limited thereto.

The term "including as an active ingredient" as sued herein refers to inclusion of an ingredient in an amount sufficient to achieve the efficacy or activity of the obtusifolin.

In an embodiment, the composition may include, based on the total weight of the composition, 0.0001 weight % to 99 weight % of the obtusifolin, the derivative thereof, or the pharmaceutically acceptable salt thereof.

In an embodiment, the amount of the obtusifolin, the derivative thereof, or the pharmaceutically acceptable salt thereof in the composition may be, based on the total weight of the composition, in a range of about 0.0001 wt % to about 90 wt %, about 0.0001 wt % to about 80 wt %, about 0.0001 wt % to about 70 wt %, about 0.0001 wt % to about 60 wt %, about 0.0001 wt % to about 50 wt %, about 0.0001 wt % to about 40 wt %, about 0.0001 wt % to about 30 wt %, about 0.0001 wt % to about 20 wt %, about 0.0001 wt % to about 10 wt %, about 0.0001 wt % to about 1 wt %, about 0.0001 wt % to about 0.1 wt %, about 0.0001 wt % to about 0.01 wt %, about 0.0001 wt % to about 0.001 wt %, about 0.001 wt % to about 99 wt %, about 0.001 wt % to about 90 wt %, about 0.001 wt % to about 80 wt %, about 0.001 wt % to about 70 wt %, about 0.001 wt % to about 60 wt %, about 0.001 wt % to about 50 wt %, about 0.001 wt % to about 40 wt %, about 0.001 wt % to about 30 wt %, about 0.001 wt % to about 20 wt %, about 0.001 wt % to about 10 wt %, about 0.001 wt % to about 1 wt %, about 0.001 wt % to about 0.1 wt %, about 0.001 wt % to about 0.01 wt %, about 0.01 wt % to about 99 wt %, about 0.01 wt % to about 90 wt %, about 0.01 wt % to about 80 wt %, about 0.01 wt % to about 70 wt %, about 0.01 wt % to about 60 wt %, about 0.01 wt % to about 50 wt %, about 0.01 wt % to about 40 wt %, about 0.01 wt % to about 30 wt %, about 0.01 wt % to about 20 wt %, about 0.01 wt % to about 10 wt %, about 0.01 wt % to about 1 wt %, about 0.01 wt % to about 0.1 wt %, about 0.1 wt % to about 99 wt %, about 0.1 wt % to about 90 wt %, about 0.1 wt % to about 80 wt %, about 0.1 wt % to about 70 wt %, about 0.1 wt % to about 60 wt %, about 0.1 wt % to about 50 wt %, about 0.1 wt % to about 40 wt %, about 0.1 wt % to about 30 wt %, about 0.1 wt % to about 20 wt %, about 0.1 wt % to about 10 wt %, about 0.1 wt % to about 1 wt %, about 1 wt % to about 99 wt %, about 1 wt % to about 90 wt %, about 1 wt % to about 80 wt %, about 1 wt % to about 70 wt %, about 1 wt % to about 60 wt %, about 1 wt % to about 50 wt %, about 1 wt % to about 40 wt %, about 1 wt % to about 30 wt %, about 1 wt % to about 20 wt %, about 1 wt % to about 10 wt %, about 10 wt % to about 99 wt %, about 10 wt % to about 90 wt %, about 10 wt % to about 80 wt %, about 10 wt % to about 70 wt %, about 10 wt % to about 60 wt %, about 10 wt % to about 50 wt %, about 10 wt % to about 40 wt %, about 10 wt % to about 30 wt %, about 10 wt % to about 20 wt %, about 20 wt % to about 99 wt %, about 20 wt % to about 90 wt %, about 20 wt % to about 80 wt %, about 20 wt % to about 70 wt %, about 20 wt % to about 60 wt %, about 20 wt % to about 50 wt %, about 20 wt % to about 40 wt %, about 20 wt % to about 30 wt %, about 30 wt % to about 99 wt %, about 30 wt % to about 90 wt %, about 30 wt % to about 80 wt %, about 30 wt % to about 70 wt %, about 30 wt % to about 60 wt %, about 30 wt % to about 50 wt %, about 30 wt % to about 40 wt %, about 40 wt % to about 99 wt %, about 40 wt % to about 90 wt %, about 40 wt % to about 80 wt %, about 40 wt % to about 70 wt %, about 40 wt % to about 60 wt %, about 40 wt % to about 50 wt %, about 50 wt % to about 99 wt %, about 50 wt % to about 90 wt %, about 50 wt % to about 80 wt %, about 50 wt % to about 70 wt %, about 50 wt % to about 60 wt %, about 60 wt % to about 99 wt %, about 60 wt % to about 90 wt %, about 60 wt % to about 80 wt %, about 60 wt % to about 70 wt %, about 70 wt % to about 99 wt %, about 70 wt % to about 90 wt %, about 70 wt % to about 80 wt %, about 80 wt % to about 99 wt %, about 80 wt % to about 90, or about 90 wt % to about 99 wt %.

In addition, the composition may include the obtusifolin, the derivative thereof, or the pharmaceutically acceptable salt thereof, at a concentration in a range of about 5 µM to about 500 µM, about 5 µM to about 400 µM, about 5 µM to about 300 µM, about 5 µM to about 200 µM, about 5 µM to about 100 µM, about 5 µM to about 50 µM, about 5 µM to about 20 µM, about 20 µM to about 500 µM, about 20 µM to about 400 µM, about 20 µM to about 300 µM, about 20 µM to about 200 µM, about 20 µM to about 100 µM, about 20 µM to about 50 µM, about 50 µM to about 500 µM, about 50 µM to about 400 µM, about 50 µM to about 300 µM, about 50 µM to about 200 µM, about 50 µM to about 100 µM, about 100 µM to about 500 µM, about 100 µM to about 400 µM, about 100 µM to about 300 µM, about 100 µM to about 200 µM, about 200 µM to about 500 µM, about 200 µM to about 400 µM, about 200 µM to about 300 µM, about 300 µM to about 500 µM, about 300 µM to about 400 µM, about 400 µM to about 500, or about 25 µM to about 200 µM. In an embodiment, when the composition includes the obtusifolin, the derivative thereof, or the pharmaceutically acceptable salt thereof, at a concentration less than the concentration above, the composition may have significantly decreased preventive or therapeutic effect on osteoarthritis, whereas, when the composition includes the obtusifolin, the derivative thereof, or the pharmaceutically acceptable salt thereof, at a concentration greater than the concentration above, the composition may have cytotoxicity or have significantly increased costs for the manufacture, thereby becoming unsuitable for use as a therapeutic agent.

The term "osteoarthritis" as used herein is also called degenerative joint disease or degenerative osteoarthritis, and refers to a disease accompanied by gradual loss of articular cartilage in local joints and secondary changes and symptoms related thereto. Osteoarthritis is a disease that causes inflammation and pain due to damage to the bones and ligaments constituting the joints due to gradual damage or degenerative changes in the cartilage protecting the joints.

The currently known treatments for osteoarthritis may include replacement arthroplasty, chondroplasty, chondral transplantation, autologous chondrocyte implantation, and the like. However, replacement arthroplasty requires joint incision so that patients feel pain and have burden and the procedure is complicated and difficult. Furthermore, replacement arthroplasty is performed only patients available for autotransplantation, and thus there are many limited areas of the treatment. Autologous chondrocyte implantation is a method whereby chondrocytes obtained from cartilage tissue collected from the normal site of a patient are cultured and proliferated in vitro as many as needed to fill the damaged cartilage site. However, this implantation also has a limitation in donor tissue, and since a surgery is required to collect tissue for implantation, the procedure is complicated and difficult. Furthermore, there are methods whereby mesenchymal stem cells are obtained from tissues including autologous bone marrow, muscle, fat, and the like and differentiated in vitro to be injected into the damaged joint cartilage site. However, when mesenchymal stem cells are differentiated into chondrocytes based on TGF-b, there is a risk that the mesenchymal stem cells may be differentiated into hypertrophic chondrocytes. Also, when mesenchymal stem cells are differentiated into BMP, there is a risk that the mesenchymal stem cells may be differentiated into osteophytes. In addition, most of drugs and health foods developed to date for osteoarthritis show a tendency to focus only on pain relief and anti-inflammatory effects, rather than on chondrocyte activity and cartilage regeneration effects that are important for the treatment of osteoarthritis.

Therefore, the composition may be able to solve problems such as side effects of conventional medicines or health foods for osteoarthritis, reduced effects of cartilage regeneration, reduced inhibitory effects of cartilage destruction, reduced therapeutic effects of fundamental osteoarthritis, or safety assurance, thereby being usefully utilized as a therapeutic agent without side effects to the human body.

In an embodiment, the composition may have one or more of the following properties:
1) decreased expression of matrix metalloproteinase 3 (MMP3), matrix metalloproteinase 13 (MMP13), or cyclooxygenase 2 (COX2);
2) decreased activity or expression of collagenase or prostaglandin $E_2$ ($PGE_2$); and
3) inhibition of signal transduction of nuclear factor kappa-light-chain-enhancer of activated B cells (NF-κB).

In an embodiment, the composition may exhibit significantly excellent effects of preventing or treating osteoarthritis by inhibiting a cartilage destruction-promoting factor and relieving an inflammatory response. In detail, the composition may inhibit activation (phosphorylation) of NF-κB signal transduction-related factors (specifically, P65) to inhibit NF-κB signal transduction, thereby alleviating an inflammatory response. Accordingly, the composition may also inhibit cartilage destruction by reducing the expression or activity of factors, such as MMP and COX2 genes, collagenase, and $PGE_2$, involved in inflammatory response or cartilage destruction.

In an embodiment, the composition may exhibit an anti-inflammatory effect, an inhibitory effect on cartilage destruction, an inhibitory effect on osteophyte formation, or an inhibitory effect on subchondral bone formation. In particular, the osteophyte refers to bony projections that are newly formed at the bone margins as a result of inflammation stimulation or the like, and the subchondral bone is known as a key factor causing a joint damage in osteoarthritis. In this regard, when considering that the composition exhibits a remarkably excellent inhibitory effect on osteophyte formation or subchondral bone formation, the composition may exhibit a remarkably excellent effect of preventing or treating osteoarthritis. Therefore, the composition may be used as a therapeutic agent for the prevention or treatment of osteoarthritis.

The term "prevention" as used herein refers to any action that inhibits or delays the onset of osteoarthritis by administration of the composition.

The term "treatment" as used herein refers to any action that improves or beneficially changes symptoms of osteoarthritis by administration of the composition.

The term "improvement" as used herein refers to any action that at least reduces parameters, for example, severity, related to the condition being treated.

The pharmaceutical composition may be characterized in the form of capsules, tablets, granules, injections, ointments, powders, or beverages, and may be also characterized in that humans are targeted.

The pharmaceutical composition may be prepared by using the active ingredient, a pharmaceutically suitable and physiologically acceptable auxiliary agent in addition to the active ingredient, and examples of the auxiliary agent are an excipient, a disintegrant, a sweetener, a binder, a coating agent, a swelling agent, a lubricant, a glidant, a flavoring agent, and the like.

For the administration, the pharmaceutical composition may be preferably formulated as a pharmaceutical composition by including one or more pharmaceutically acceptable carriers in addition to the active ingredient.

Formulations of the pharmaceutical composition may be granules, powders, tablets, coated tablets, capsules, suppositories, solutions, syrups, juices, suspensions, emulsions, drops, or injectable solutions. For example, for formulation in the form of tablets or capsules, the active ingredient may be combined with an oral and non-toxic pharmaceutically acceptable carrier, such as ethanol, glycerol, water, and the like. In addition, when desired or needed, suitable binders, lubricants, disintegrants, and color-developers may also be included in a mixture. Examples of the suitable binder are, although not limited thereto, starch, gelatin, glucose, or natural sugar, such as beta-lactose, corn sweetener, natural and synthetic gums, such as acacia, tragacanth, or sodium oleate, sodium stearate, magnesium stearate, sodium benzoate, sodium acetate, sodium chloride, and the like. Examples of the disintegrant are, although not limited thereto, starch, methyl cellulose, agar, bentonite, xanthan gum, and the like.

In the case where the pharmaceutical composition is formulated as a liquid solution, the pharmaceutically acceptable carrier is sterile and biocompatible, and may include saline, sterile water, Ringer's solution, buffered saline, albumin injection solution, dextrose solution, and maltodextrin solution, glycerol, or ethanol, or a mixture of one or more of these components. Also, other conventional additives, such as an antioxidant, a buffer, a bacteriostat, and the like, may be added as needed. In addition, a diluent, a dispersant, a surfactant, a binder, and a lubricant may be additionally added to formulate the pharmaceutical composition as an injectable form, such as an aqueous solution, a suspension, an emulsion, and the like, a pill, a capsule, a granule, or a tablet. Furthermore, the pharmaceutical composition may be preferably formulated depending on each disease or component using an appropriate method in the art.

The pharmaceutical composition may be administered orally or parenterally. In the case of parenteral administration, the administration may be performed by intravenous injection, subcutaneous injection, intramuscular injection, intraperitoneal injection, transdermal administration, or the like, and the oral administration may be preferable.

A suitable dosage of the pharmaceutical composition may vary depending on factors, such as a formulation method, an administration method, a patient's age, weight, gender, and pathological condition, food, administration time, an administration route, an excretion rate, and response sensitivity. A skilled physician may easily determine and prescribe an effective dosage for the desired treatment or prevention.

The pharmaceutical composition may be formulated into a unit dosage form or prepared in a multi-dose container by formulating a pharmaceutically acceptable carrier and/or an excipient according to the method easily carried out by a person having ordinary skill in the art to which the present disclosure pertains. Here, the dosage form may be a solution in an oily or aqueous medium, a suspension, an emulsion, an extract, a powder, a granule, a tablet, or a capsule, and may further include a dispersant or a stabilizer.

One or more embodiments include a food composition for improving or preventing osteoarthritis including obtusifolin, a derivative thereof, or a pharmaceutically acceptable salt thereof.

The obtusifolin may be a compound having the structure of Formula 1:

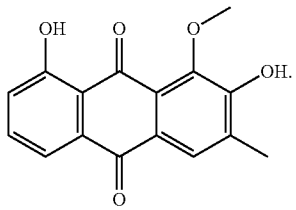

Formula 1

The term "pharmaceutically acceptable salt" as used herein is the same as defined in connection with the pharmaceutical composition. In addition, the term "pharmaceutically acceptable salt" as used herein may be used interchangeably with the term "salt acceptable as food" or may be a concept including "salt acceptable as food".

The term "salt acceptable as food" as used herein may be the same as defined in connection with the "pharmaceutically acceptable salt", or may be defined a salt in which the obtusifolin is combined with an acid or base acceptable as food within the scope of the above-described definition.

The food composition may be formulated in the same manner as the pharmaceutical composition to be used as a functional food or added to various foods. The foods to which the food composition may be added may include, for example, beverages, alcohol, confectionery, diet bars, dairy products, meat, chocolate, pizza, ramen, other noodles, gums, ice cream, vitamin complexes, health supplements, and the like.

The foods may be prepared in all forms, such as a functional food, a nutritional supplement, a health food, and a food additive. For example, as a health food, the obtusifolin, the derivative thereof, or the pharmaceutically acceptable salt thereof may be prepared in the form of tea, juice, or drink for drinking, or may be granulated, encapsulated, or powdered for consumption. In addition, as a functional food, beverages (including alcoholic beverages), fruits and fruit processed foods (e.g., canned fruit, bottled food, jam, marmalade, etc.), fish, meat prepared fish, and processed meat (e.g., ham, sausage, corned beef, etc.), breads and noodles (e.g., udon noodles, soba noodles, ramen, spaghetti, macaroni, etc.), fruit juice, various drinks, cookies, syrup, dairy products (e.g., butter, cheese, etc.), edible vegetable oils and fats, margarine, vegetable protein, retort food, frozen food, various seasonings (e.g., soybean paste, soy sauce, sauce, etc.), and the like may be prepared by adding the obtusifolin, the derivative thereof, or the pharmaceutically acceptable salt thereof.

The food composition may include, as an active ingredient, not only the obtusifolin, the derivative thereof, or the pharmaceutically acceptable salt thereof, or a pharmaceutically acceptable salt thereof, but also an ingredient that is commonly added during the preparation of feeds. For example, the food composition may include protein, carbohydrate, fat, nutrients, seasonings, or flavoring agents. Examples of the carbohydrate include: monosaccharides such as glucose, fructose, and the like; disaccharides, such as maltose, sucrose, oligosaccharides, and the like; polysaccharides including conventional sugars, such as dextrin and carbohydrate; or sugar alcohol, such as xylitol, sorbitol, erythritol, and the like. As the flavoring agent, a natural flavoring agent (e.g., taumatine, stevia extract (such as rebaudioside A, glycyrrhizin, and the like)), or a synthetic flavoring agent (e.g., saccharin, aspartame, and the like) may be used. For example, when the food composition is prepared as a drink or beverage, the food composition may further include citric acid, fructose corn syrup, sugar, glucose, acetic acid, malic acid, fruit juice, various plant extracts, or the like, in addition to the obtusifolin, the derivative thereof, or the pharmaceutically acceptable salt thereof.

Another aspect provides a health functional food comprising a food composition for improving or preventing osteoarthritis, the food composition comprising, as an active ingredient, obtusifolin, a derivative thereof, or a pharmaceutically acceptable salt thereof. The health functional food refers to a food prepared by adding the obtusifolin, the derivative thereof, or the pharmaceutically acceptable salt thereof to food materials, such as beverages, teas, spices, gums, confectioneries, or the like, or a food prepared by using the obtusifolin, the derivative thereof, or the pharmaceutically acceptable salt thereof in encapsules, powders, or suspensions. It is a food expected to exhibit specific health effects when consumed. However, unlike general drugs, a food is used as a raw material, and thus there are no side effects that may occur when taking the drug for a long period of time. Therefore, the health functional food may be very useful as being ordinarily consumed.

In an embodiment, the health functional food may be in the form of pills, tablets, capsules, or beverages.

Regarding the health functional food, addition amounts of the obtusifolin, the derivative thereof, or the pharmaceutically acceptable salt thereof may vary depending on a type of a target health functional food, and thus may not be uniformly defined. However, when added within a range that does not impair the original taste of the food, the addition amounts of the obtusifolin, the derivative thereof, or the pharmaceutically acceptable salt thereof may be in a range of about 0.01 wt % to about 50 wt %, preferably, about 0.01 wt % to about 20 wt %, with respect to the health functional food. In addition, when the health functional food is in the form of pills, granules, tablets, or capsules, the addition amounts of the obtusifolin, the derivative thereof, or the pharmaceutically acceptable salt thereof may be in a range of about 0.01 wt % to about 100 wt %, preferably, about 0.01 wt % to about 80 wt % or about 0.01 wt % to about 50 wt %.

Among the terms or elements mentioned in connection with the food composition or the health functional food, those mentioned the same as in the description of the pharmaceutical composition are understood to be the same as mentioned in the description of the pharmaceutical composition above.

Another aspect provides a composition for anti-inflammation, inhibition of cartilage destruction, inhibition of osteophyte formation, or inhibition of subchondral bone formation, the composition comprising, as an active ingredient, obtusifolin, a derivative thereof, or a pharmaceutically acceptable salt thereof.

The inflammation may refer to inflammation occurring in musculoskeletal or connective tissue, for example, joints, bones, cartilage, or spinal cord. Therefore, the composition for anti-inflammation may be a composition for inhibiting, alleviating, or preventing inflammation occurring in musculoskeletal or connective tissue.

The composition may be used to prepare pharmaceuticals, quasi-drugs, foods, or the for the prevention, improvement, or treatment of osteoarthritis.

Among the terms or elements mentioned in connection with the composition, those mentioned the same as in the description of the pharmaceutical composition, food composition, or health functional food are understood to be the same as mentioned in the description of the pharmaceutical composition, food composition, or health functional food above.

Another aspect provides a method for preventing or treating osteoarthritis, the method comprising administering obtusifolin, a derivative thereof, or a pharmaceutically acceptable salt thereof to a subject.

Another aspect provides a method for inhibiting inflammation, cartilage destruction, osteophyte formation, or subchondral bone formation, the method comprising administering obtusifolin, a derivative thereof, or a pharmaceutically acceptable salt thereof to a subject The inflammation may refer to inflammation occurring in musculoskeletal or connective tissue, for example, joints, bones, cartilage, or spinal cord.

The subject may refer to a target in need of the prevention or treatment of osteoarthritis, and more specifically, may refer to mammals such as a human or a non-human primate, a mouse, a rat, a dog, a cat, a horse, and cattle.

Regarding the method, the administering to the subject may include administering a composition that includes, as an active ingredient, obtusifolin, a derivative thereof, or a pharmaceutically acceptable salt thereof, such as a pharmaceutical composition, to the subject.

Regarding the method, the administering to the subject may include administering an effective amount of a composition (for example, a pharmaceutical composition) that includes, as an active ingredient, obtusifolin, a derivative thereof, or a pharmaceutically acceptable salt thereof, to the subject.

The term "effective amount" as used herein refers to an amount of an active ingredient or composition (for example, a pharmaceutical composition) that induces a biological or medical response in a tissue system, an animal, or a human, as considered by a researcher, a veterinarian, a physician, or other clinicians, The effective amount may refer to an amount that induces alleviation of symptoms of a disease or disorder in consideration.

Regarding the method, it is apparent to those skilled in the art that an effective amount and the number of administration of: the obtusifolin, the derivative thereof, or the pharmaceutically acceptable salt thereof; or the composition (for example, a pharmaceutical composition) including the same as an active ingredient will vary depending on a desired effect. Therefore, the optimal amount to be administered may be easily determined by those skilled in the art, and may be adjusted depending in various factors including the type of disease, the severity of the disease, the amounts of active ingredients and other components included in the composition, the type of formulation, the patient's age, weight, general health condition, gender, and diet, the administration time, the administration route, the secretion rate of the composition, the treatment period, the drugs being simultaneously used, and the like.

In an embodiment, regarding the method, when the obtusifolin, the derivative thereof, or the pharmaceutically acceptable salt thereof is administered once a day or several times a day, it may be administered at a dose, based on a body weight of the subject, in a range of about 0.0001 g/kg to about 100 g/kg, about 0.0001 g/kg to about 10 g/kg, about 0.0001 g/kg to about 1 g/kg, about 0.0001 g/kg to about 0.1 g/kg, about 0.0001 g/kg to about 0.01 g/kg, about 0.0001 g/kg to about 0.001 g/kg, about 0.001 g/kg to about 100 g/kg, about 0.001 g/kg to about 10 g/kg, about 0.001 g/kg to about 1 g/kg, about 0.001 g/kg to about 0.1 g/kg, about 0.001 g/kg to about 0.01 g/kg, about 0.01 g/kg to about 100 g/kg, about 0.01 g/kg to about 10 g/kg, about 0.01 g/kg to about 1 g/kg, about 0.01 g/kg to about 0.1 g/kg, or about 0.005 g/kg to about 0.5 g/kg.

Regarding the method, the obtusifolin, the derivative thereof, or the pharmaceutically acceptable salt thereof; or the composition (for example, a pharmaceutical composition) including the same as the active ingredient may be administered in a general manner via an oral, rectal, intravenous, intra-arterial, intraperitoneal, intramuscular, intrasternal, transdermal, topical, intraocular, or intradermal route.

Among the terms or elements mentioned in connection with the method, those mentioned the same in the description of the pharmaceutical composition, food composition, health functional food, or composition are understood to be the same as mentioned in the description of the pharmaceutical composition, food composition, health functional food, or composition above.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 1 is a graph showing the results of measuring the cytotoxicity of obtusifolin;

FIG. 2A is an image showing the results of measuring the expression levels of transcriptomes of MMP3, MMP13, and COX2 in chondrocytes treated with IL-1β and obtusifolin;

FIG. 3A is an image showing the results of measuring the activation (phosphorylation) levels of p38, JNK, and p65 in chondrocytes treated with IL-1β;

FIG. 3B is an image showing the results of measuring the activation (phosphorylation) level of p65 in chondrocytes treated with IL-1β and obtusifolin;

FIG. 3C is a graph showing the results of measuring the activation (phosphorylation) level of p65 in chondrocytes treated with IL-1β and obtusifolin;

FIG. 5A is an image of Safranin O-staining showing the results confirming the inhibitory effects of obtusifolin on cartilage destruction after administration of obtusifolin to mice that have undergone DMM surgery or sham-operated surgery;

FIG. 5B is a graph showing the results of analyzing Osteoarthritis Research Society International (OARSI) grades after administration of obtusifolin to mice that have undergone DMM surgery or sham-operated surgery;

FIG. 5C is a graph showing the results of measuring the degree of osteophyte formation after administration of obtusifolin to mice that have undergone DMM surgery or sham-operated surgery;

DETAILED DESCRIPTION

Figure 2B:
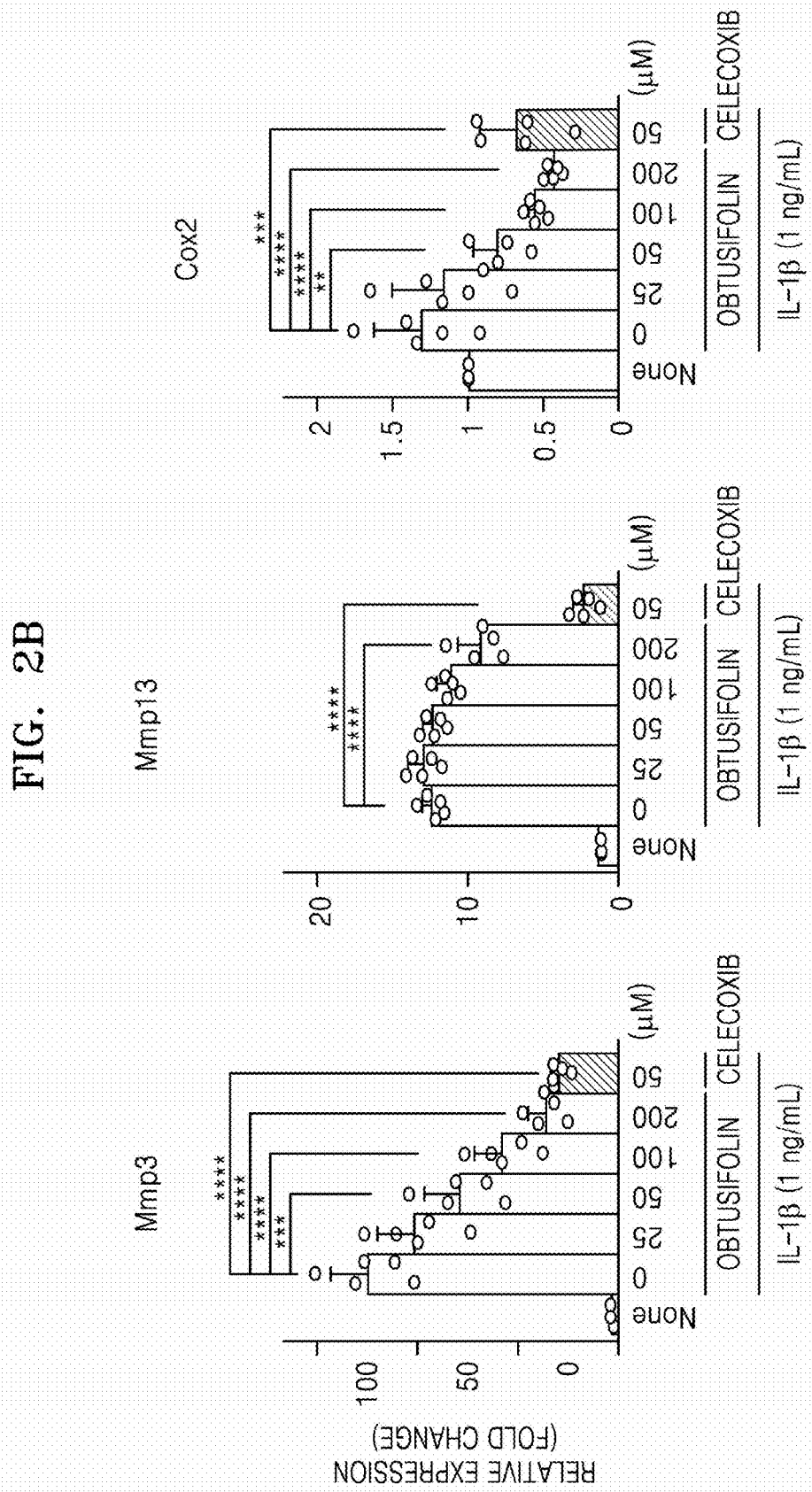
FIG. 2B is a graph showing the results of measuring the expression levels of transcriptomes of MMP3, MMP13, and COX2 in chondrocytes treated with IL-1β and obtusifolin.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, the present disclosure will be described in detail with reference to Experimental Examples and Examples below. However, these Experimental Examples and Examples are provided for illustrative purposes only, and the scope of the present disclosure is not limited thereto.

In addition, unless specifically defined herein, all scientific and technical terms used in the present specification may have the same meaning as commonly understood by those skilled in the art to which the present disclosure belongs.

Reference Example: Experimental Materials and Methods

1. Preparation of Obtusifolin

Obtusifolin used for the experiment was identified to have a structure of Formula 1, a molecular formula of $C_{16}H_{12}O_5$, and a molecular weight of about 284.26 g/mol:

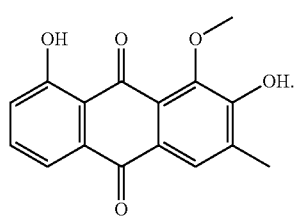

Formula 1

2. Primary Culture of Mouse Articular Chondrocytes and Preparation for Animal Experiment Mouse chondrocytes isolated from femur and tibial plateau were obtained from ICR mice of 5-days old. Cells were cultured in Dulbecco's Modified Eagle's medium to which about 10% fetal bovine serum and about 1% penicillin/streptomycin, and then grown in an incubator under conditions maintained with about 5% $CO_2$ and a temperature of about 37° C. C57BL/6 mice (male, 10-weeks old, weighing about 18 g to 20 g, and n=5) were purchased from DBL (Chungcheongbuk-do, South Korea). The C57BL/6 mice were housed at a temperature of about 23° C. and exposed to a light-dark cycle of about 12 hours. Food and water were provided regularly. All animal experiments were performed under the approval of the Ajou University Animal Care and Use Committee.

3. In Vitro Treatment of Chondrocyte and Reagent

Interleukin 1 beta (IL-1β) purchased from GenScript (Piscataway, NJ, USA) was dissolved in purified water. Obtusifolin and celecoxib were purchased from Sigma-Aldrich (St. Louis, MO, USA). Primary chondrocytes of the mice were cultured for 4 days under conditions of a temperature of about 37° C. and about 5% $CO_2$. Afterwards, IL-1β (about 1 ng/mL) and either of obtusifolin or celecoxib were treated and cultured for about 24 hours. Then, the cultured chondrocytes were collected after about 5 days. To confirm the signal transduction pathway regulated by obtusifolin, the chondrocytes were pre-treated with obtusifolin or celecoxib and cultured for about 24 hours. Afterwards, before collecting of the chondrocytes, the chondrocytes were treated with IL-1β (about 1 ng/mL), and then cultured in a serum-free medium for about 10 minutes.

4. Lactate Dehydrogenase-Assay

The primary chondrocytes were treated with obtusifolin (0 μM, about 25 μM, about 50 μM, about 100 μM, and about 200 μM) and cultured for about 24 hours. Then, the supernatant of the culture was collected and allowed for a reaction using a LDH-cytotoxicity assay kit (K311-400; BioVision). According to the recommendations provided by the kit manufacturer, values were measured.

5. Transcription and Protein Analysis

Chondrocyte RNAs were isolated using Trizol and chloroform. Cell proteins and lipids were disrupted by Trizol, and RNA was isolated by layering with chloroform. As such, the total RNA isolated from the primary chondrocytes was reverse transcribed into cDNA using an ImProm-II™ Reverse Transcriptase kit (Promega, A3803). Primers and temperature conditions for each gene are provided in Table 1. Transcription levels were quantified by qRT-PCR (ABI, Beverley, UK; StepOnePlus Real-Time PCR System). Primers for target genes and temperature conditions used in the qPCR are provided in Table 1. By using a LIPA lysis buffer containing about 150 mM NaCl, about 1% NP-40, about 50 mM Tris pH 8.0, about 0.2% SDS, and about 5 mM NaF and additional protease/phosphatase inhibitor cocktail (Roche, Madison, WI, USA), total proteins were extracted from the primary cultured chondrocytes. The extracted proteins were separated by size using an acrylamide gel, and primary antibodies used after transfer are as follows:

mouse anti-Erk1/2 (sc-514302; Santa Cruz), rabbit anti-COX2 (ab52237; Abcam), rabbit anti-P65 (8242S; Cell signaling technology), rabbit anti-pP65 (3033S; Cell signaling technology), rabbit anti-JNK (9252S; Cell signaling technology), rabbit anti-p-JNK (9251S; Cell signaling technology), rabbit anti-p38 (cst9212; Cell signaling technology), and rabbit anti-pp38 (cst92159; Cell signaling technology).

Here, as a loading control group, Erk1/2 was used. Band intensity was quantified by densitometry (AlphaEase FC 4.0; Alpha Innotech).

6. Analysis of $PGE_2$ and Collagenase and Analysis of Reporter Gene $PGE_2$ production was evaluated using a $PGE_2$ Immunoassay Kit (R & D System, Minneapolis, Minnesota, USA). Primary articular chondrocytes of mouse were seeded in a 96-well plate (about 2×10⁴ cells/well). The level of secreted $PGE_2$ in the primary chondrocytes of mouse treated with obtusifolin and IL-1β (about 1 ng/mL) was measured from the total cell lysates. By using an EnzCheck Gelatinase/Collagenase Assay kit (Molecular Probes, Carlsbad, CA, USA), total collagenase activity of the articular chondrocytes cultured in a medium conditioned with obtusifolin and IL-1β (about 1 ng/mL) was measured. The collagenase activity was quantified using a VICTOR X3 microplate reader (PerkinElmer, Waltham, MA, USA) at Ex/Em=490/530 nm according to the protocol provided by the manufacturer. The NF-κB reporter gene structure was transfected with the articular chondrocytes of mouse through LipofectAMINE Plus (Invitrogen, Carlsbad, CA, USA). After culturing the transfected cells in a complete medium for about 24 hours, luciferase activity was evaluated using an analysis kit (Promega, Madison, WI, USA), and the evaluated activity was normalized by β-galactosidase.

7. Osteoarthritis (OA)-Induced Mouse and Oral Administration

According to a known technique, destabilization of the medial meniscus (DMM) surgery was performed on a mouse of about 10 week old to induce OA. Here, a Sham-operated mouse was used as a control group. After 4 weeks of the DMM surgery, the mouse was orally administered with obtusifolin (at a dose of about 10 mg/kg, about 50 mg/kg, or about 100 mg/kg) for about 6 weeks. Here, the obtusifolin was administered in a dissolved state in about 90% 1×PBS (CBP007B; LPS), about 5% DMSO (D2650-5×5 ML; Sigma), and about 5% tween 80 (9005-65-6; Sigma). Here, a group to which only 1×PBS was administered was used as a comparison group.

8. Histological Analysis

A mouse cartilage sample obtained from the mouse undergoing the DMM surgery was fixed about 4% para-formaldehyde followed by dehydration for about 2 weeks in about 0.5 mol/L EDTA (pH 8.0), to decalcify. The decalcified cartilage sample was embedded in paraffin, and sections of a resulting paraffin block were continuously cut at intervals of about 50 μm first, and then to a thickness of about 5 μm. The sectioned sample was fixed on a glass slide and hydrated to various grades of ethanol free from paraffin and xylene. The cartilage destruction was measured by Safranin O staining and scored using an Osteoarthritis Research Association International (OARSI) grading system.

9. Statistics

Data values were expressed as mean±SEM after repeated experiments. Along with Dunnett's post-hoc multiple comparison test, Student's t-test and one-way ANOVA were used to estimate statistical significance (*$P<0.05$, $P<0.01$, *$P<0.001$, and ****$P<0.0001$). All analyzes were performed using GraphPad Prism 7 (GraphPad, San Diego, CA, USA). Histological data were quantified based on an ordinal grading system including OARSI grades, subchondral bone plate thickness scores, and osteophyte grades, using non-parametric statistical methods. By calculating probability directly from the result data, a statistical test was performed.

TABLE 1

| Gene | Origin | Strand | Primer sequences | Size (bp) | annealing temperature (° C.) |
|---|---|---|---|---|---|
| MMP3 | Mouse | S (sense) | 5'-CTGTGTGT GGTTGTGTGCT CATCCTAC-3' (SEQ ID NO: 1) | 350 | 58 |
| | | As (antisense) | 5'-GGCAAATCCG GTGTATAATT CACAATC-3' (SEQ ID NO: 2) | | |
| MMP13 | Mouse | S | 5'-TGATGGAC CTTCTGGTCTT CTGG-3' (SEQ ID NO: 3) | 473 | 58 |
| | | AS | 5'-CATCCACATGG TTGGGAAGTTC T-3' (SEQ ID NO: 4) | | |
| COX2 | Mouse | S | 5'-GGTCTGGTGC CTGGTCTGAT GAT-3' (SEQ ID NO: 5) | 724 | 65 |
| | | As | 5'-GTCCTTTCAA GGAGAATGGT GC-3' (SEQ ID NO: 6) | | |
| Gapdh | Mouse | S | 5'-TCACTGC CACCCAGAAG AC-3' (SEQ ID NO: 7) | 450 | 55 |
| | | As | 5'-TGTAGGC CATGAGGTCC AC-3' (SEQ ID NO: 8) | | |
| qMMP3 | Mouse | S | 5'-TCCTGATG TTGGTGGCTTC AG-3' (SEQ ID NO: 9) | 102 | 60 |
| | | AS | 5'-TGTCTTGG CAAATCCGGTG TA-3' (SEQ ID NO: 10) | | |
| qMMP13 | Mouse | S | 5'-CTTCTTCTT GTT-GAGCTGGAC TC-3' (SEQ ID NO: 11) | 173 | 60 |
| | | AS | 5'-CTGTG-GAGG TCACTGTAGAC T-3' (SEQ ID NO: 12) | | |
| qCOX2 | Mouse | S | 5'-TT-CAACACA CTCTAT-CACTGG C-3' (SEQ ID NO: 13) | 271 | 60 |

TABLE 1-continued

| Gene | Origin Strand | Primer sequences | Size (bp) | annealing temperature (° C.) |
|------|---------------|------------------|-----------|------------------------------|
|      | AS            | 5'-AGAAGCGTT TGCGGTACTCA T-3' (SEQ ID NO: 14) |  |  |

Experimental Example 1: Confirmation of Obtusifolin Effect on Osteoarthritis (OA)

1-1. Confirmation of Cytotoxicity of Obtusifolin

In this experimental example, cytotoxicity of obtusifolin was measured using a lactate dehydrogenase-assay to determine whether obtusifolin affected chondrocytes. Detailed experimental methods were described in Reference Example.

FIG. 1 is a graph showing the results of measuring the cytotoxicity of obtusifolin.

As a result, as shown in FIG. 1, it was confirmed that obtusifolin did not exhibit cytotoxicity at a concentration of about 200 μM or less.

1-2. Confirmation of Inhibitory Effect of Obtusifolin on OA-Related Factor

In this experimental example, to confirm inhibitory effects of obtusifolin on OA-related factors, the expression or activity levels of transcriptomes and proteins of MMP and COX2 in the obtusifolin-treated chondrocytes were measured. Celecoxib, which is used as a conventional therapeutic agent for OA, was used as a comparison group.

In detail, chondrocytes treated with pro-inflammatory cytokine, IL-1β (about 1 ng/mL), for about 24 hours were treated with obtusifolin (about 0 μM to about 200 μM) or Celecoxib (about 50 μM). Then, in the resulting chondrocytes, the expression levels of matrix metalloproteinase 3 (MMP3), matrix metalloproteinase 13 (MMP13), and cyclooxygenase 2 (COX2) were measured by RT-PCR and qRT-PCR. In addition, the activity level of collagenase and the expression level of prostaglandin ($PGE_2$) were measured. Detailed experimental methods were described in Reference Example.

FIGS. 2A and 2B are an image (FIG. 2A) and a graph (FIG. 2B), each showing the results of measuring the expression levels of transcriptomes of MMP3, MMP13, and COX2 in the chondrocytes treated with IL-1β and obtusifolin.

Figure 2C:
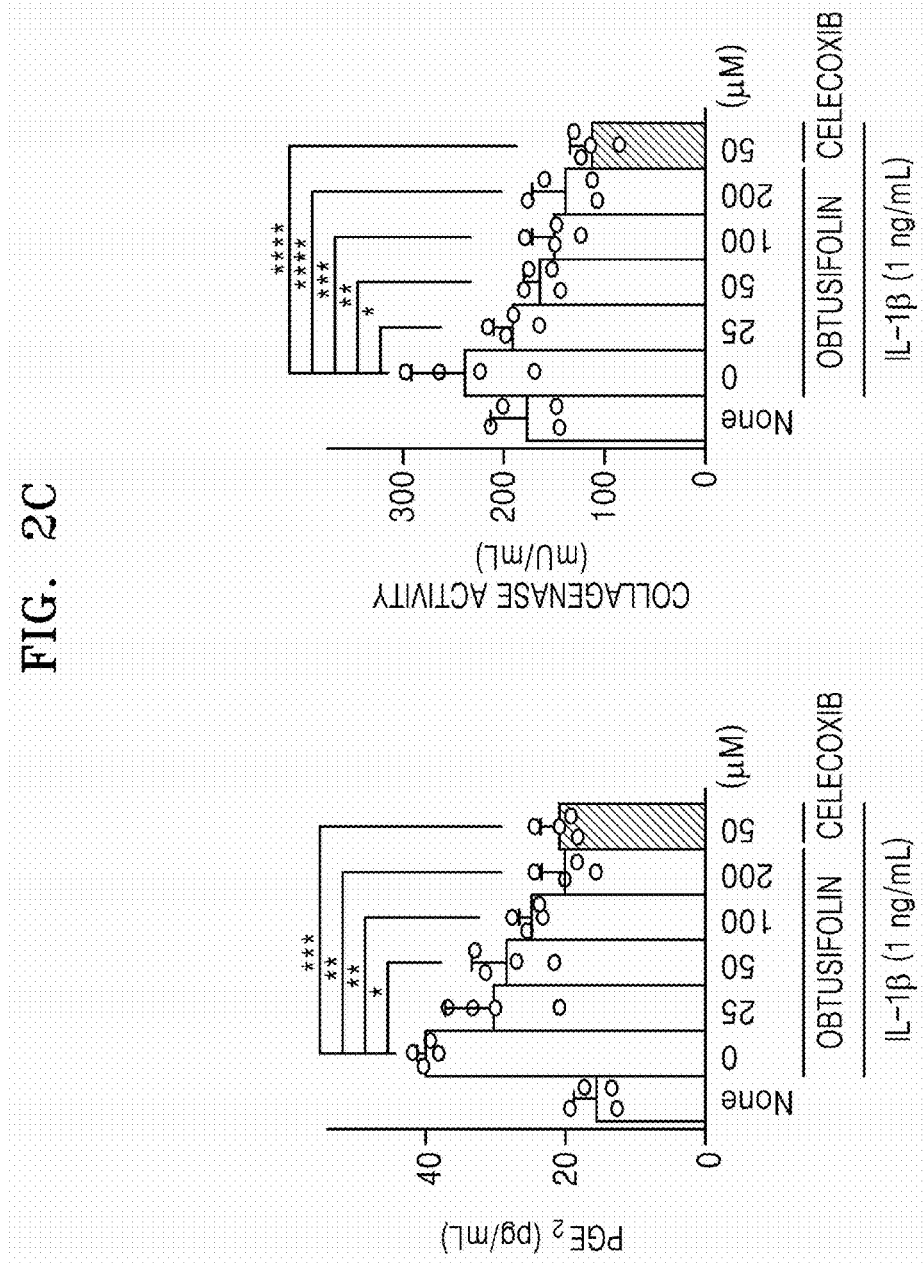
FIG. 2C shows graphs showing the results of measuring the expression level of $PGE_2$ and the activity levels of collagenase in chondrocytes treated with IL-1β and obtusifolin.

FIG. 2C shows graphs showing the results of measuring the expression level of $PGE_2$ and the activity level of collagenase in the chondrocytes treated with IL-1β and obtusifolin.

Consequently, as shown in FIGS. 2A and 2B, it was confirmed that, when the chondrocytes were treated with the pro-inflammatory cytokine, IL-1β, the expression of catabolic factors such as MMP3, MMP13, and COX2 was increased, whereas, when the chondrocytes were treated with obtusifolin, the expression of MMP3, MMP13, and COX2 increased by IL-1β was decreased again. In particular, it was confirmed that the expression levels of MMP3 and COX2 were decreased in a dose-dependent manner of obtusifolin.

In addition, as shown in FIG. 2C, it was confirmed that the activity of collagenase and the expression of $PGE_2$ in the chondrocytes were decreased in a dose-dependent manner of obtusifolin.

Furthermore, when the chondrocytes were treated with obtusifolin at a concentration in a range of about 100 μM to about 200 μM, the greatest effects of reducing the expression or activity of the transcriptomes of MMP and COX2, collagenase, and $PGE_2$ were exhibited. In detail, it was confirmed that the obtusifolin used at a concentration in a range of about 100 μM to about 200 μM exhibited the same or similar level of effects as Celecoxib which is a conventional OA therapeutic agent.

It is known that, when the expression of COX2 was increased, $PGE_2$ increased, causing an inflammatory response. As the frequency of the inflammatory response increased, the expression of MMP increased and the activity of collagenase increased, thereby promoting the cartilage destruction. In this regard, the results of this experimental example showed that obtusifolin inhibited the cartilage destruction by inhibiting the expression or activity of factors involved in the inflammatory response or the cartilage destruction, thereby implying that obtusifolin exhibited therapeutic effects on OA.

1-3. Confirmation of Inhibitory Effect of Obtusifolin on OA-Related NF-κB Signal Transduction OA is known to be caused by inflammation or cartilage decomposition through specific signal transduction pathways. In detail, it is known that, when chondrocytes are exposed to pro-inflammatory cytokines such as IL-1β, NF-κB cell signal transduction molecules including p38, JNK, and p65 are activated by phosphorylation.

Therefore, in this experimental example, to confirm the inhibitory effects of obtusifolin on the OA-related NF-κB signal transduction, the activation (phosphorylation) levels of p38, JNK, and p65 in the chondrocytes treated with IL-1β and obtusifolin were measured. Here, Celecoxib, which is used as a conventional therapeutic agent for OA, was used as a comparison group.

In detail, the chondrocytes treated with the pro-inflammatory cytokine, IL-1β (about 1 ng/mL), were collected, and the phosphorylation levels of p38, JNK, and p65 were measured through Western blotting. In addition, the chondrocytes treated with obtusifolin (about 0 μM to 200 μM) or Celecoxib (about 50 μM) were cultured for about 24 hours, and then additionally treated with IL-1β (about 1 ng/mL) and cultured for about 10 minutes. The chondrocytes were collected after the culture, and the phosphorylation level of p65 was measured through Western blotting and densitometry. Detailed experimental methods were described in Reference Example.

FIG. 3A is an image showing the results of measuring the activation (phosphorylation) levels of p38, JNK, and p65 in the chondrocytes treated with IL-1β.

FIGS. 3B and 3C are an image (FIG. 3B) and a graph (FIG. 3C), each showing the results of measuring the activation (phosphorylation) level of p65 in the chondrocytes treated with IL-1β and obtusifolin.

Consequently, as shown in FIG. 3A, it was confirmed that, when the chondrocytes were treated with IL-1β which is a pro-inflammatory cytokine, p38, JNK, and p65 were phosphorylated and then activated. However, as shown in FIGS. 3B and 3C, it was confirmed that, as the concentration of obtusifolin for the treatment with the chondrocytes increased, the phosphorylation of P65 was inhibited in the chondrocytes.

Furthermore, when the chondrocytes were treated with obtusifolin at a concentration in a range of about 100 μM to about 200 μM, the greatest effects of inhibiting the phosphorylation of P65 were exhibited. In detail, it was confirmed that the obtusifolin used at a concentration in a range of about 100 μM to about 200 μM inhibited the phosphorylation of P65 at the same or similar level to that of Celecoxib which is a conventional OA therapeutic agent.

The results of this Experimental Example showed that the obtusifolin reduced the activity (phosphorylation) of P65 in the chondrocytes and accordingly inhibited the NF-κB signal transduction that caused OA, thereby implying that the obtusifolin exhibited effects of treating OA by alleviating the inflammatory response.

1-4. Confirmation of Inhibitory Effect of Obtusifolin on Cartilage Destruction Induced by DMM Surgery In this section, to confirm inhibitory effects of obtusifolin on cartilage destruction, which was especially induced by DMM surgery, a mouse model experiment was performed as shown in FIG. 4.

Figure 4:
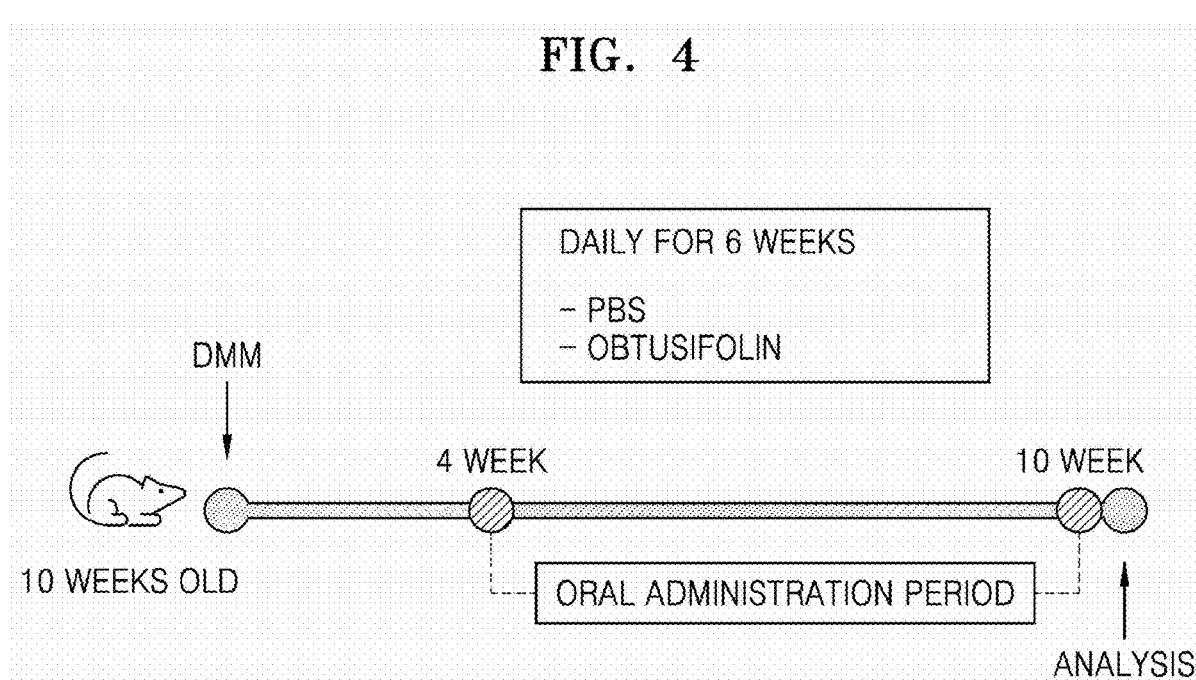
FIG. 4 is a schematic diagram showing a mouse model experimental procedure for confirming the inhibitory effects of obtusifolin on cartilage destruction that is induced by destabilization of medial meniscus (DMM) surgery.

FIG. 4 is a schematic diagram showing a mouse model experimental procedure to confirm the inhibitory effects of obtusifolin on the cartilage destruction, which was especially induced by DMM surgery.

In detail, the DMM surgery or shame surgery was performed on mice, and after about 4 weeks of the surgery, obtusifolin (about 10 mg/kg, about 50 mg/kg, or about 100 mg/kg) was administered to each mouse every day for 6 weeks. Then, cartilage was collected from each mouse, and Safranin O staining was performed on a cartilage cross section. The degree of cartilage destruction was analyzed by analyzing images obtained after the staining. In detail, the OARSI grades, the degree of osteophyte formation, and a thickness of the subchondral bone were measured. Here, a mouse model experimental group in which PBS was administered instead of obtusifolin was used as a comparison group. Detailed experimental methods were described in Reference Example.

Figure 5D:
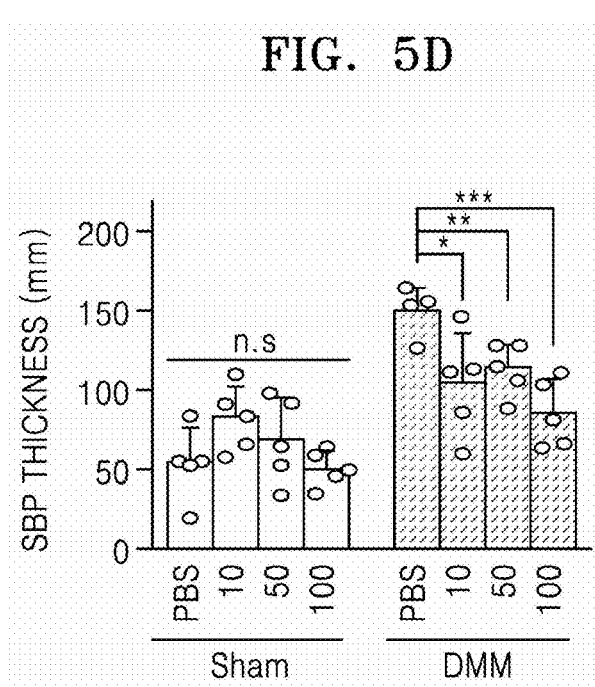
FIG. 5D is a graph showing the results of measuring the thickness of subchondral bone after administration of obtusifolin to mice that have undergone DMM surgery or sham-operated surgery.

FIGS. 5A to 5D are diagrams showing the results of confirming the inhibitory effects of obtusifolin on the cartilage destruction after administered to the mouse that have undergone the DMM surgery or shame surgery (wherein FIG. 5A is an image of the Safranin O staining; FIG. 5B is a graph showing the results of analyzing the OARSI grades; FIG. 5C is a graph showing the results of measuring the degree of osteophyte formation; and FIG. 5D is a graph showing the results of measuring the thickness of the subchondral bone).

Consequently, as shown in FIGS. 5A to 5D, it was confirmed that no difference in the effects according to the dose concentration of obtusifolin was found in the mice undergoing the sham surgery, whereas the degree of cartilage destruction decreased in a dose-dependent manner with the administration of obtusifolin in the mice undergoing the DMM surgery. In detail, it was confirmed that, in the mice undergoing the DMM surgery, the formation of osteophytes, which are osseous protuberances, newly formed at the bone edge due to inflammatory stimulation or the like was reduced in a dose-dependent manner with the administration of obtusifolin (FIG. 5C); the thickness of the subchondral bone, which is a key factor causing joint damage in OA (degenerative arthritis) was reduced (FIG. 5D); and ultimately the OA grades were decreased (FIG. 5B).

Through this experimental example, it was confirmed that obtusifolin may significantly inhibit the cartilage destruction induced by the DMM surgery. Accordingly, it was also confirmed that obtusifolin was able to exhibit an effect of treating OA.

Through the experimental examples above, it was confirmed that obtusifolin was able to exhibit a therapeutic effect on OA.

Figure 6:
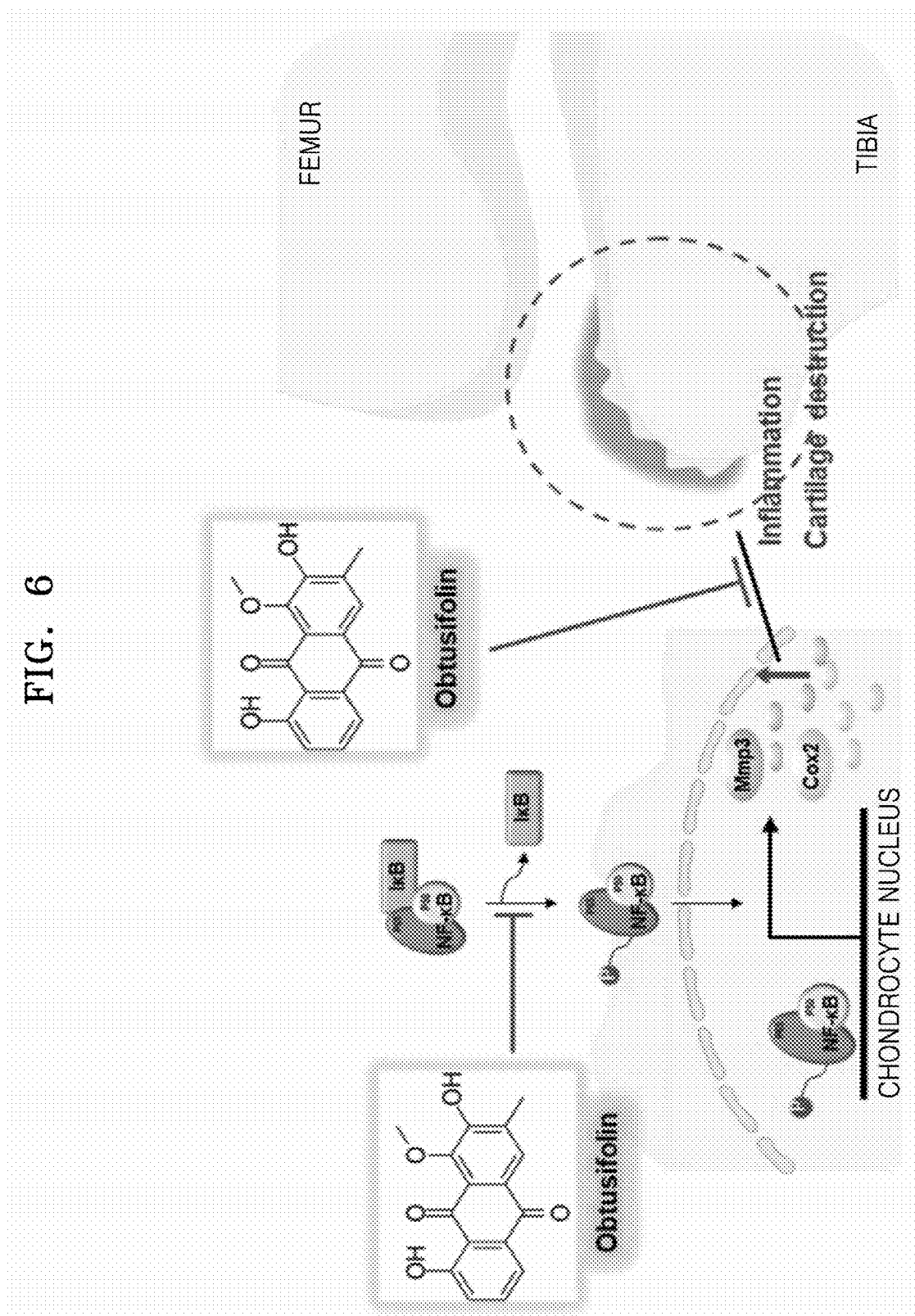
FIG. 6 is a schematic diagram illustrating a mechanism of action of therapeutic effects of obtusifolin on osteoarthritis.

FIG. 6 is a schematic diagram illustrating a mechanism of action of therapeutic effects of obtusifolin on OA.

In detail, as shown in FIG. 6, it was confirmed that obtusifolin was able to alleviate the inflammatory response by inhibiting the NF-κB signal transduction by inhibiting the activation (phosphorylation) of the NF-κB signal transduction-related factors. Accordingly, it was also confirmed that obtusifolin was able to inhibit the cartilage destruction by reducing the expression or activity of factors, such as MMP and COX2 genes, collagenase, and $PGE_2$, involved in the inflammatory response or cartilage destruction. As a result, it was confirmed that obtusifolin exhibited effects of significantly alleviating OA by inhibiting the cartilage destruction or the formation of osteophytes or subchondral bones. The results above suggest that obtusifolin may be used as a therapeutic agent for treating OA.

The foregoing descriptions are only for illustrating the present disclosure, and it will be apparent to a person having ordinary skill in the art to which the present disclosure pertains that the embodiments disclosed herein can be easily modified into other specific forms without changing the technical spirit or essential features. Therefore, it should be understood that Examples described herein are illustrative in all respects and are not limited.

According to the one or more embodiments described above, a composition may exhibit a significantly excellent effect of preventing or treating osteoarthritis by inhibiting factors promoting cartilage destruction and alleviating an inflammatory response. In detail, obtusifolin included in the composition may be able to alleviate an inflammatory response by inhibiting NF-κB signal transduction by inhibiting activation (phosphorylation) of NF-κB signal transduction-related factors. Accordingly, the composition may also inhibit cartilage destruction by reducing the expression or activity of factors, such as MMP and COX2 genes, collagenase, and $PGE_2$, involved in inflammatory response or cartilage destruction. Therefore, considering the effects of the composition on the inhibition of cartilage destruction or inhibition of formation of osteophytes or subchondral bones, the composition may be utilized as a therapeutic agent for the prevention or treatment of osteoarthritis.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A method for preventing or treating osteoarthritis, the method comprising:
   administering obtusifolin, a derivative thereof, or a pharmaceutically acceptable salt thereof to a subject.

* * * * *